United States Patent [19]

Young et al.

[11] Patent Number: 5,847,202
[45] Date of Patent: Dec. 8, 1998

[54] RACEMIZATION PROCESS FOR OPTICALLY ACTIVE CARBOXYLIC ACIDS OR SALTS OR ESTERS THEREOF

[75] Inventors: Robert E. Young, West Columbia; Hao V. Phan, Columbia, both of S.C.; Thanikavelu Manimaran; Ronald C. Zumstein, both of Baton Rouge, La.

[73] Assignee: Albemarle Corporation, Richmond, Va.

[21] Appl. No.: 955,543

[22] Filed: Oct. 22, 1997

Related U.S. Application Data

[63] Continuation-in-part of Ser. No. 661,233, Jun. 10, 1996, abandoned.

[51] Int. Cl.⁶ .................................................. C07C 55/00
[52] U.S. Cl. ........................... 562/401; 560/56; 560/105
[58] Field of Search ............................... 562/401; 560/56, 560/105

[56] References Cited

U.S. PATENT DOCUMENTS

| | | | |
|---|---|---|---|
| 3,686,183 | 8/1972 | Dyson | 260/284 |
| 4,245,116 | 1/1981 | Ohno et al. | 562/401 |
| 4,246,164 | 1/1981 | Felder et al. | 260/501.17 |
| 4,851,444 | 7/1989 | Sunshine et al. | 514/570 |
| 4,877,620 | 10/1989 | Loew et al. | 424/451 |
| 5,015,764 | 5/1991 | Manimaran et al. | 562/401 |
| 5,221,765 | 6/1993 | Patil et al. | 562/401 |
| 5,235,095 | 8/1993 | Kadkhodayan et al. | 560/218 |
| 5,254,720 | 10/1993 | Wu | 560/105 |
| 5,315,026 | 5/1994 | Wu | 560/105 |
| 5,332,834 | 7/1994 | Bhattacharya et al. | 48/339.1 |

FOREIGN PATENT DOCUMENTS 5910545  1/1984  Japan.

*Primary Examiner*—Samuel Barts
*Attorney, Agent, or Firm*—Philip M. Pippenger

[57] ABSTRACT

Optically active carboxylic acids, salts or esters, such as the profen-type compounds, are racemized in the presence by nitrogenous bases such as methylbenzylamine by heating an aqueous solution of such optically active compounds in the presence of a suitable excess of an alkali metal hydroxide relative to the amount optically active carboxylic compound present in the solution. The process not only enables conversion of inactive or undesirable enantiomers of compounds such as naproxen or ibuprofen into a usable, desirable enantiomers in an efficient and economical manner, but avoids conversion of the nitrogenous base into amide. Thus the deleterious consequences of amide formation are avoided.

27 Claims, No Drawings

RACEMIZATION PROCESS FOR OPTICALLY ACTIVE CARBOXYLIC ACIDS OR SALTS OR ESTERS THEREOF

REFERENCE TO RELATED APPLICATION

This application is a continuation-in-part of our prior application Ser. No. 08/661,233, filed Jun. 10, 1996 now abandoned.

TECHNICAL FIELD

This invention relates to a process for converting an enantiomeric form of certain aliphatic carboxylic acids into a racemic mixture of enantiomers. This invention more specifically relates to racemization of one of the enantiomers of profen-type carboxylic acids, salts or esters.

BACKGROUND

Profen-types of compounds are typically defined as propionic acids (or esters) bearing at least one aromatic substituent, usually α- to the carboxylic function. These acids have an asymmetric carbon atom (the carbon atom adjacent to the carbonyl group) that typically produces a racemic mixture of these acids, i.e., a mixture of both the (+) and (−) or dextro and levo rotary forms. For example, ibuprofen [(2-(4-isobutylphenyl)propionic acid)], a commercially and pharmaceutically important chemical, is typically produced and sold as the racemic mixture. Other profen drugs are also produced as racemates and administered in this form. However, it is known that the physiological utility of the racemic mixtures is almost exclusively focused on one enantiomer, the other having either no effect or even diminishing the effect of the active enantiomer. Thus the S(+) form of ibuprofen is active in reducing inflammation and in providing an analgesic effect. See, for example, U.S. Pat. Nos. 4,851,444 and 4,877,620. The R(−) enantiomer is devoid of activity for these indications, although it is, in part, converted in vivo into the S(+) compound. Other profen pharmaceuticals, e.g., 2-(6-methoxy-2-naphthyl) propionic acid (naproxen), are only prescribed as the single enantiomer.

Disposal of the undesired enantiomer is not environmentally or economically desirable. Thus an efficient method of converting the inactive or undesirable enantiomer of these carboxylic acids into the other usable, desirable enantiomer is an commercially important objective.

U.S. Pat. No. 3,686,183 to Dyson describes the racemization of α-substituted predominately d- or l-arylacetic acids by heating with an optically active nitrogenous base at a suitable temperature for a suitable time until racemization occurs.

U.S. Pat. No. 5,221,765 to Patil et al. describes the racemization of optically active carboxylic acids or esters thereof by heating an aqueous solution of the optically active carboxylic acid or ester with a catalytic amount of an aliphatic, aromatic or mixed aliphatic-aromatic tertiary amine for a time sufficient to racemize the acid or ester. In the Examples of the patent the process is conducted in the presence of S-methylbenzyl amine. Loss of ibuprofen due to amide formation is experienced.

Amide formation is deleterious for several reasons. First of all, amide formation results in loss of portions of both chiral amine and chiral acid content of the reaction mixture. Besides being wasteful, such loss is costly as both such materials are expensive. Secondly, the amide products are relatively high molecular weight materials which readily form solid deposits which tend to accumulate in the reaction system and storage vessels and which can cause pluggage of lines or other similar operational problems when conducting the process on a commercial scale. Thirdly, the accumulation of such deposits necessitates purging the system of such solids, and disposal of the waste products in a suitable manner, operations which add to the plant operating costs.

It would be desirable to provide a novel, commercially practicable process whereby the inactive or undesirable enantiomer of these carboxylic acids may be converted into the other usable, desirable enantiomer, especially if the conversion of one enantiomer of these carboxylic acids into the other enantiomer could be conducted in an efficient and economical manner without undesirable amide formation.

This invention makes it possible to achieve these objectives.

SUMMARY OF THE INVENTION

This invention provides a method for racemizing in the presence of an organic nitrogenous base, typically a chiral organic nitrogeneous base such as a chiral amine, one of the enantiomers, or an enantiometrically enriched mixture, of an optically active compound of the formula:

$$R^1R^2R^3CCOOZ \qquad (I)$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is a hydrogen atom, an alkali metal cation, a hydrocarbyl group or a cation of a nitrogenous base such as an amine cation, or a combination of two or more of the foregoing. For convenience, compounds of formula (I) are sometimes referred to herein as "Carboxylic Compounds". The method comprises mixing a sufficient amount of an inorganic alkali metal base having a base strength greater than that of the nitrogenous base to provide a suitable excess of alkali metal cation in the solution relative to the Carboxylic Compound (s) present in the solution, and heating the resultant aqueous solution at a temperature and for a time sufficient to racemize the Carboxylic Compound while in solution. In this operation no precipitation occurs, and not only is the Carboxylic Compound or mixture of Carboxylic Compounds racemized, but no appreciable conversion of the organic nitrogenous base to organic amide occurs. The excess of alkali metal base present in the solution may be thought of as a catalytic quantity of free alkali metal base. Viewed in this way, the method comprises heating an aqueous solution of the Carboxylic Compound and a nitrogenous base (in whatever form they may exist while in the solution) at a temperature of from about 80° C. to about 200° C. in the presence of an effective catalytic amount of a free alkali metal hydroxide (in whatever form it may exist while in the solution) for a time sufficient to racemize the Carboxylic Compound.

As noted above, in this process the original enantiomer, or enantiometrically enriched mixture, of the Carboxylic Compound(s) is racemized without measurable conversion of amine moieties to amide moieties. Consequently, the racemization process of this invention avoids loss of valuable components present in the initial mixture being treated, notably chiral amine and chiral acid content of the reaction mixture. Besides avoiding such waste and the economic penalty incurred when such waste occurs, the process avoids formation of amide products which typically are relatively high molecular weight materials. As noted above, such materials readily form solid deposits which tend to accumulate in the reaction system and storage vessels and which can cause pluggage of lines or other similar operational problems when conducting the process on a commercial scale. Moreover, the process eliminates the need for periodically purging the system of such deposits, and the need for and problems associated with disposal of such waste products in a suitable manner, operations which further add to the plant operating costs.

The process is applicable to racemization of any original mixture corresponding to the above formula. The addition of the alkali metal base (typically alkali metal hydroxide or alkali metal oxide, which forms the hydroxide in situ) and application of heat results in neutralization of free carboxyl groups, if any, by alkali metal cations, the displacement of the amine cation by alkali metal cation and/or the saponification of carboxylic ester groups (if a hydrolyzable ester was used). In all cases the resultant mixture will contain a nitrogenous base such as an amine, and an effective quantity of "free" alkali metal hydroxide catalyst, i.e., an amount of alkali metal hydroxide over and above that theoretically consumed in neutralizing free carboxylic acid groups, displacing amine cations, and/or saponifying ester groups (whichever is applicable by virtue of the composition of the original enantiomer, or enantiometrically enriched mixture, of Carboxylic Compound(s) charged to the reaction vessel for racemization).

Thus in the practice of this invention, enough strong inorganic alkali metal base is mixed with the initial aqueous mixture containing Carboxylic Compound and organic nitrogenous base so that the resulting solution contains a total amount of strong alkali metal (in whatever form it is actually in) such that if the alkali metal were entirely ionized, the solution would contain an excess of the strong alkali metal cation relative to the total amount of Carboxylic Compound present in the solution. It will be understood that because of differences in extent of ionization from compound to compound and the possibility that various chemical equilibria may exist in the resulting solution, the actual forms of the denoted substances at any given instant of time cannot be stated with absolute certainty. Thus the "excess" of "strong alkali metal cation" assumes 100% ionization of all strong alkali metal present in the solution, whether or not all of it is in fact ionized.

FURTHER DESCRIPTION OF THE INVENTION

One of the enantiomeric forms (or an enantiomerically enriched mixture) of such carboxylic acids, esters or salts is used as a starting material and is subjected to the process of this invention whereby conversion of one enantiomer to the other is effected. The process functions to achieve a racemic mixture of the enantiomers, i.e., it is a racemization process.

The carboxylic acids, salts and esters useful in the process of this invention have the formula (I) above. Preferably, Z in formula (I) is a hydrogen atom, an alkali metal cation (most preferably sodium or potassium), a $C_1$ to $C_6$ linear or branched alkyl group, or a cation of a nitrogenous base such as a univalent amine cation. Likewise, in formula (I), $R^1$, $R^2$, and $R^3$ are different and preferably are selected from among the following univalent groups: a hydrogen atom; $C_1$ to $C_6$ linear or branched alkyl (e.g., methyl or ethyl); $C_1$ to $C_6$ linear or branched haloalkyl (e.g., chloromethyl, fluoromethyl, chloroethyl, fluoroethyl, difluoromethyl, trifluoromethyl); aralkyl (e.g., benzyl, phenethyl); cycloalkyl (e.g., cyclopropyl, cyclobutyl, cyclopentyl, cyclohexyl); alkyl-substituted cycloalkyl (e.g., methylcyclohexyl, dimethylcyclopentyl); $C_6$ to $C_{18}$ aryl (e.g., phenyl, 1-naphthyl, 2-naphthyl, 2-biphenylyl, 3-biphenylyl, 4-biphenylyl, anthryl, fluoryl, tetrahydronaphthyl); alkyl-substituted aryl (e.g., tolyl, xylyl, trimethylphenyl, butylphenyl, and especially isobutylphenyl, 4-ethyl-1-naphthyl, 1,6-dimethyl-2-naphthyl, 4'-butyl-4-biphenylyl, 6-ethyl-2-biphenylyl); aryl substituted with $C_1$ to $C_4$ alkylthio, or $C_1$ to $C_4$ alkoxy, or cyano or halo, such as fluoro or chloro, especially fluoro-substituted biphenylyl groups; $C_1$ to $C_6$ linear or branched alkoxy (e.g., methoxy, ethoxy, propoxy, or butoxy); $C_6$ to $C_{18}$ aryloxy (e.g., phenoxy or phenoxy substituted with, for example, methyl, dimethyl, butyl or isobutyl, or phenoxy substituted with $C_1$ to $C_4$ alkylthio, or $C_1$ to $C_4$ alkoxy, or cyano or halo; $C_1$ to $C_6$ alkythio (e.g., methylthio, ethylthio); $C_3$ to $C_8$ cycloalkylthio; $C_6$ to $C_{18}$ arylthio; $C_6$ to $C_{18}$ arylcarbonyl (e.g., benzoyl); $C_4$ to $C_8$ cycloalkenyl (e.g., cyclopentenyl, cyclohexenyl); halo (e.g., fluoro or chloro); and $C_4$ to $C_{12}$ heteroaryl (e.g., furyl, pyrrolyl, thienyl).

One group of preferred compounds of formula (I) are those in which $R^1$, $R^2$ and Z are as previously defined, and $R^3$ is a biphenylyl group (especially where one phenyl group is in the 4-position of the other phenyl group, i.e., a 4-biphenylyl or p-biphenylyl group) wherein either ring is, or both rings are, substituted by (i) $C_1$ to $C_4$ linear or branched alkyl, (ii) $C_1$ to $C_4$ linear or branched alkoxy, and/or (iii) halo.

Compounds of formula (I) in which $R^1$, $R^2$ and Z are as previously defined, and $R^3$ is a naphthyl group (either 1-naphthyl or 2-naphthyl or both) wherein at least the ring (and most preferably the only ring) other than the ring to which the asymmetric carbon atom is bonded is substituted by (i) $C_1$ to $C_4$ linear or branched alkyl, (ii) $C_1$ to $C_4$ linear or branched alkoxy, and/or (iii) halo, is another group of preferred starting materials.

Still another group of preferred compounds of formula (I) are those in which $R^1$, $R^2$ and Z are as previously defined, and $R^3$ is a phenyl group wherein the ring is substituted by (i) $C_1$ to $C_4$ linear or branched alkyl, (ii) $C_1$ to $C_4$ linear or branched alkoxy, and/or (iii) halo.

Compounds of formula (I) wherein $R^1$, $R^2$ and Z are as previously defined, and $R^3$ is a phenyl group substituted by a $C_7$ to $C_{18}$ aroyl group (especially a benzoyl group) constitutes yet another group of preferred starting materials.

Practice of this invention enables improvements in overall synthesis procedures which can be used for producing such finished end products as 2-(6-methoxy-2naphthyl)propionic acid (also known as naproxen), 2-(4-isobutylphenyl) propionic acid (also known as ibuprofen), 2-(3-fluoro-4-biphenylyl)propionic acid (also known as flurbiprofen), 2-(3-benzoylphenyl)propionic acid (also known as ketoprofen).

The process of this invention is conducted in an aqueous medium at a temperature of from about 80° C. to about 200° C., preferably in the range of about 100° C. to about 170° C., and most preferably at about 120° C. to about 140° C. The optimum temperature conditions depend to some extent upon the particular optically active material being used in the racemization process. If necessary, this can readily be determined by conducting a few pilot experiments with the particular material to be racemized. The various reactions involved in the process take place in solution and no precipitate formation is involved.

The strong inorganic alkali metal base (hydroxide or precursor thereof) in the form as introduced into the mixture to be subjected to racemization pursuant to this invention can be any alkali metal hydroxide or alkali metal oxide having a base strength greater than that of the nitrogeneous base(s) present in the solution. Preferred from the cost-effectiveness standpoint are sodium hydroxide, potassium hydroxide, sodium oxide, potassium oxide and any mixture or combination of these. However, sodium carbonate, potassium carbonate, or other water-soluble strong inorganic alkali metal bases can be used. In the presence of the water, ionization will take place, and in the case of the oxide, conversion to hydroxide occurs. Thus during the reaction the inorganic base is in whatever form into which it has been converted as a natural consequence of being introduced into the aqueous mixture to be subjected to the present racemization process.

A suitable amount of the strong inorganic alkali metal base, preferably a hydroxide or an oxide of sodium or potassium, is introduced into or otherwise mixed with the mixture. To avoid erroneous interpretations, let it be understood that the word "introduced" is not used in a limitive sense to mean that the strong inorganic base must be added to the mixture. Rather "introduced" is used in the sense that the materials being used are brought together. How the materials are gotten into the racemization mixture and whatever form they assume when in the mixture are both immaterial, so long as they get there to perform in accordance with this invention.

The amount of inorganic alkali metal base introduced should be sufficient to provide an excess of alkali metal cation over the amount of the Carboxylic Compound(s) present in the mixture being treated. For example, if the Carboxylic Compound(s) present is/are in the form of a combination of free acid and amine salt, the amount of strong alkali metal base introduced will be theoretically sufficient to displace the amine, to neutralize the free acid, and also leave an excess of alkali metal cation in the aqueous system. If the Carboxylic Compound(s) present is/are in the form of a combination of amine salt and, say, sodium or potassium salt, the amount of strong alkali metal base is theoretically sufficient to displace the amine and also leave an excess of alkali metal cation in the aqueous system. Thus in this case the actual amount of the strong alkali metal base introduced into the mixture will be only that amount theoretically needed to displace the amine and provide the excess of alkali metal cation in the solution. If the Carboxylic Compound(s) present is/are in the form of a saponifiable ester, the amount of strong alkali metal base introduced will be sufficient theoretically to saponify the ester and leave the excess of alkali metal cation in the aqueous system.

It will be seen that the excess of the strong inorganic alkali metal base used in the process apparently serves as a catalyst to effect the racemization. Thus, without being bound by theory, it is theorized that the strong inorganic alkali metal base serves two fundamental functions. Firstly, it converts (through neutralization of free acid, and/or displacement of amine salt and/or saponification of ester) all of the Carboxylic Compound(s) present into the alkali metal salt (at least theoretically, as the salt may be ionized at least to some extent in the solution). Secondly, it provides the excess of strong alkali metal base over theoretical to serve as a racemization catalyst.

Water is the principal diluent used in the process, and ordinarily it is not necessary to introduce any other diluent or solvent. However if an ancillary diluent or solvent is employed it should be miscible with water at the concentration employed, and should be inert to the reactants and not cause precipitation of the alkali metal base introduced into the system.

To summarize, a suitable quantity of the alkali metal hydroxide or precursor thereof is introduced into the mixture in which racemization is to be effected. This quantity is an amount at least sufficient to cause, under the racemization conditions to be used, conversion of at least a portion of undesired enantiomer into desired enantiomer. In general, if a portion of the enantiomer(s) to be racemized is initially present in the system in acid form and the remainder of the enantiomer(s) is present as amine salt(s), the amount of alkali metal base introduced into the reaction mixture is in excess of the amount theoretically consumed in displacing amine cations and in neutralizing the free acids present in the system. If the enantiomer(s) to be racemized is/are initially present in the system only in the form of salts of amine, the amount of alkali metal base introduced into the reaction mixture is in excess of the amount theoretically consumed in displacing amine and forming the alkali metal salt. Similarly, if the enantiomers to be racemized are initially present in the system in ester form, the amount of alkali metal base introduced into the reaction mixture is in excess of the amount theoretically consumed in saponifying the esters. Generally speaking, the reaction mixtures used as the starting materials for racemization in the practice of this invention will initially contain on a weight basis from about 10 to about 50% of acid, up to about 25% of nitrogenous base, an amount of alkali metal hydroxide in the range of up to about 25%, with the balance (to 100%) being water.

In the racemization of 2-(6-methoxy-2-naphthyl) propionic acid enantiomers and similar compounds, the presence of too much free alkali metal hydroxide such as sodium hydroxide and/or potassium hydroxide can result in hydrolysis of the alkoxy group under the racemization temperature conditions. Thus, when conducting the process using 2-(6methoxy-2-naphthyl)propionic acid enantiomers or other compounds of formula (I) above that can be degraded under the racemization conditions by exposure to excessive amounts of free alkali metal hydroxide, the catalytically effective (excess) amount of free sodium hydroxide and/or potassium hydroxide in the racemization solution is in the range of up to about 1.0 mole per mole (chemical equivalent) of optically active enantiomers present in such solution. Preferably the amount of such free (excess) sodium and/or potassium hydroxide in the racemization solution is in the range of about 0.2 to about 0.4 mole per mole or chemical equivalent of optically active enantiomers present in such solution. A typical naproxen reaction mixture will contain about 30 to about 40%, e.g., about 35%, naproxen (as naproxen sodium); about 2 to about 5%, e.g., about 3%, methylbenzyl amine; about 1 to about 3%, e.g., about 1.5%, sodium hydroxide, and the balance to 100% being essentially water. Such a reaction mixture is a preferred starting material for use in the racemization process of this invention.

In conducting the racemization process of this invention, it is desirable to agitate the reaction mixture to ensure intimate contact among the components of the system. Preferably the racemization is conducted in a closed reaction vessel under autogenous pressure. Reaction times will generally vary inversely with reaction temperature, but should be selected to afford sufficient time for the racemization to proceed to the extent desired within the capabilities of the process under the set of circumstances involved. The racemization mixture will usually be maintained at the selected temperature(s) for a period in the range of from about 1 to about 24 hours.

Optically active nitrogenous bases co-present in the racemization solution are usually used in earlier stages of processing are thus normally are carried along from the earlier stages of processing. Among such asymmetric optically active nitrogenous basesare, for example, those referred to in U.S. Pat. No. 3,686,183 to Dyson, especially at Column 5, lines 9–27 thereof, incorporated herein by reference. A preferred chiral amine is methylbenzylamine.

The following examples illustrate the practice and advantages of this invention.

EXAMPLE 1

A reaction mixture containing a relatively low content of the (S)-enantiomeric form of 2-(6-methoxy-2-naphthyl) propionic acid (naproxen) was formed by charging 800 grams of racemic naproxen, 81.5 grams of sodium hydroxide 1000 grams of water and 1420 grams of toluene to a 5-liter flask. While stirring this mixture at a temperature of 55° C., 175 grams of (S)-methylbenzylamine was added over a period of 35 minutes. After 4 more hours of stirring the resultant mixture at 55° C., the aqueous and organic phases were separated by decantation, and the organic phase was washed twice with 1-liter portions of water. The original aqueous cut and these two water washes were combined and found to contain 37.5% in the (S)-enantiomeric form. From this combined aqueous mixture, 2006 grams of water was stripped off.

To conduct the racemization pursuant to this invention, the bottoms remaining from the stripping step were charged to a 2-liter autoclave containing 41 grams of sodium hydroxide, and the resultant mixture was stirred at 130° C. for 15 hours. The naproxen portion from this racemization was found to contain 50% in the (S)-enantiomeric form. It was also determined that no amide formation occurred during the racemization operation.

EXAMPLE 2

The procedure of Example 1 is repeated except that the racemization temperature is 120° C. and the racemization operation is conducted for 23 hours.

EXAMPLE 3

The procedure of Example 1 is again repeated except that the racemization operation is conducted for 3.5 hours at 140° C.

It is to be understood that terms referring anywhere in the specification or claims hereof to a chemical compound or substance, whether the term is used in the singular or plural, are used in the sense that it is a substance having (A) the composition specified herein that it would have if it were not already in a solution or in admixture with something else specified herein, or (B) the composition specified herein that it has prior to introduction into the mixture being formed or used. Thus in the case of (A), prior to unification and/or treatment with one or more other materials at a time before being acted upon in the present process, the ingredient or component would have been in the chemical form specified. In the case of (B), prior to mixing with one or more other materials, the ingredient or component is in the chemical form specified. It matters not what chemical changes, transformations and/or complexations, if any, take place in the mixture or medium used as such changes, transformations and/or complexations are the natural result of bringing the specified ingredients or components together and subjecting the resultant system to the conditions specified herein. It is also to be clearly understood that since the reactions described herein are for the most part conducted in aqueous systems, ionization, especially of inorganic materials such as alkali metal hydroxide, will occur. Thus the term "free alkali metal hydroxide" as used herein does not mean or imply that the compound exists in the non-ionized form of alkali metal hydroxide. Rather the term is used to refer to the amount of alkali metal hydroxide that is theoretically present in the solution (e.g., as alkali metal cations and hydroxyl anions) over and above that theoretically necessary to convert into alkali metal cations all of Z of formula (I) above that is not in theory already alkali metal cation. Thus "free" refers to a theoretically calculated or calculatable quantity and not to a physical or chemical state or form. In addition it is to be understood and appreciated that the alkali metal hydroxide can be used as such in forming the racemization solution (e.g., as by adding it to the aqueous medium) or it can be formed in situ in the racemization solution (e.g., as by adding alkali metal oxide to the aqueous medium). In either case the resultant alkali metal hydroxide will be ionized when in solution, and the resultant ions will then do whatever they will normally do in the selected system of the type referred to herein under the selected conditions of the type described herein. Further, even though the claims hereinafter may refer to components or compounds in the present tense ("comprises", "is", etc.), such reference does not denote that the component or compound must presently exist in that form. It may be ionized or otherwise transformed by virtue of the material(s) with which it is associated in accordance with the claim, and such material(s) in turn may be transformed by virtue of the material(s) with which it is or they are associated in accordance with the claim. Therefore, such reference in the present tense merely serves as a way of referring to the substance when in its ordinary state. Those skilled in the art will, of course, readily understand all such matters.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A method for racemizing in the presence of one or more organic nitrogenous bases, one of the enantiomers, or an enantiometrically enriched mixture, of an optically active carboxylic compound of the formula:

$$R^1R^2R^3CCOOZ \qquad (I)$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is a hydrogen atom, an alkali metal cation, a hydrocarbyl group, a cation of a nitrogenous base or a combination of two or more of the foregoing, said method comprising:

heating an aqueous solution of the optically active carboxylic compound and the organic nitrogenous base in the presence of a sufficient amount of an inorganic alkali metal base having a base strength greater than that of the organic nitrogenous base to provide an excess of alkali metal cation in the solution relative to the amount of said optically active carboxylic compound present in the solution, at one or more temperatures and for a time sufficient to racemize the optically active carboxylic compound while in solution, said optically active carboxylic compound, said organic nitrogenous base, and said inorganic alkali metal base being in whatever form or forms they may exist while in the solution.

2. A method according to claim 1 wherein the one or more temperatures is/are in the range of from about 80° C. to about 200° C.

3. A method according to claim 1 wherein the inorganic alkali metal base used is sodium hydroxide and/or potassium hydroxide, and wherein said excess of alkali metal cation in said solution is in the range of up to about 1.0 mole per mole of said optically active compound present in said solution.

4. A method according to claim 3 said excess is in the range of about 0.2 to about 0.4 mole per mole of said optically active compound present in said solution.

5. A method according to claim 1 wherein $R^1$ is a hydrogen atom, $R^2$ is alkyl, and $R^3$ is alkylaryl, alkoxyaryl or haloaryl and said nitrogenous base is methylbenzylamine.

6. A method according to claim 5 wherein Z is (i) a hydrogen atom, (ii) a sodium cation, (iii) a methylbenzylamine cation, or (iv) a combination of any two or all three of (i), (ii), and (iii), and wherein the inorganic alkali metal base used is sodium hydroxide.

7. A method according to claim 5 wherein Z is (i) a hydrogen atom, (ii) a potassium cation, (iii) a methylbenzylamine cation, or (iv) a combination of any two or all three of (i), (ii), and (iii), and wherein the inorganic alkali metal base used is potassium hydroxide.

8. A method according to claim 6 wherein the excess of sodium cation is in the range of about 0.2 to about 0.4 mole per mole of said optically active compound present in said solution.

9. A method according to claim 7 wherein the excess of potassium cation is in the range of about 0.2 to about 0.4 mole per mole of said optically active compound present in said solution.

10. A method according to claim 1 wherein said temperature is in the range of about 100° C. to about 170° C.

11. A method according to claim 1 wherein said temperature is in the range of about 120° C. to about 140° C.

12. A method for racemizing in the presence of one or more organic nitrogenous bases, one of the enantiomers, or an enantiometrically enriched mixture, of an optically active carboxylic compound of the formula:

$$R^1R^2R^3CCOOZ \qquad (I)$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is a hydrogen atom, an alkali metal cation, a hydrocarbyl group, a cation of a nitrogenous base or a combination of two or more of the foregoing, said method comprising:

a) mixing with an aqueous solution containing said optically active carboxylic compound and said one or more organic nitrogenous bases, a sufficient amount of an inorganic alkali metal base having a base strength greater than that of said one or more organic nitrogenous bases to provide an excess of alkali metal cation in the solution relative to the amount of said optically active carboxylic compound present in the solution; and b) heating the resultant aqueous solution at one or more temperatures and for a time sufficient to racemize the optically active carboxylic compound while in solution without appreciable conversion of the organic nitrogenous base to organic amide occurring.

13. A method according to claim 12 wherein the alkali metal constituent of the inorganic alkali metal base used in a) is sodium and/or potassium, and wherein the excess of sodium and/or potassium cation in said solution is in the range of up to about 1.0 mole per mole of said optically active compound present in said solution.

14. A method according to claim 12 wherein the inorganic alkali metal base used in a) is sodium hydroxide or potassium hydroxide, and wherein the excess of sodium or potassium cation in said solution is in the range of about 0.2 to about 0.4 mole per mole of said optically active compound present in said solution.

15. A method according to claim 12 wherein $R^1$ is a hydrogen atom, $R^2$ is alkyl, and $R^3$ is alkylaryl, alkoxyaryl or haloaryl and said nitrogenous base is methylbenzylamine.

16. A method according to claim 12 wherein Z is (i) a hydrogen atom, (ii) a sodium cation, (iii) a methylbenzylamine cation, or (iv) a combination of any two or all three of (i), (ii), and (iii), and wherein the inorganic alkali metal base used is sodium hydroxide.

17. A method according to claim 16 wherein the excess of sodium cation is in the range of about 0.2 to about 0.4 mole per mole of said optically active compound present in said solution.

18. A method according to claim 17 wherein $R^1$ is a hydrogen atom, $R^2$ is alkyl, and $R^3$ is alkylaryl, alkoxyaryl or haloaryl and said nitrogenous base is methylbenzylamine.

19. A method according to claim 12 wherein said temperature is in the range of about 100° C. to about 170° C.

20. A method according to claim 12 wherein $R^1$ is a hydrogen atom, $R^2$ is alkyl, and $R^3$ is alkylaryl, alkoxyaryl or haloaryl and said organic nitrogenous base is methylbenzylamine; wherein the inorganic alkali metal base used in a) is sodium hydroxide or potassium hydroxide; wherein the excess of sodium or potassium cation in said solution is in the range of about 0.2 to about 0.4 mole per mole of said optically active compound present in said solution; and wherein said temperature is in the range of about 100° C. to about 170° C.

21. A method according to claim 12 wherein $R^1$ is a hydrogen atom, $R^2$ is alkyl, and $R^3$ is alkylaryl, alkoxyaryl or haloaryl; wherein said organic nitrogenous base is methylbenzylamine; wherein the inorganic alkali metal base used in a) is sodium hydroxide; wherein the excess of sodium cation in said solution is in the range of about 0.2 to about 0.4 mole per mole of said optically active compound present in said solution; and wherein said temperature is in the range of about 100° C. to about 170° C.

22. A method according to claim 21 wherein said temperature is in the range of about 120° C. to about 140° C.

23. A method for racemizing in the presence of one or more organic nitrogenous bases, 2-(6-methoxy-2-naphthyl) propionic acid and/or salt(s) thereof in which less than 50% thereof is the (S)-enantiomeric form thereof, said method comprising:

a) mixing with an aqueous solution containing said propionic acid and/or salt(s) thereof, and said one or more organic nitrogenous bases, a sufficient amount of an inorganic alkali metal base having a base strength greater than that of said one or more organic nitrogenous bases to provide an excess of alkali metal cation in the solution relative to the amount of said propionic acid and/or salt(s) thereof present in the solution; and b) heating the resultant aqueous solution at one or more temperatures and for a time sufficient to racemize said propionic acid and/or salt(s) thereof while in solution without appreciable conversion of organic nitrogenous base to organic amide occurring.

24. A method according to claim 23 wherein said organic nitrogenous base is methylbenzylamine.

25. A method according to claim 23 wherein the inorganic alkali metal base is sodium hydroxide or potassium hydroxide, or both; wherein the excess of sodium and/or potassium cation in the solution relative to the amount of said propionic acid and/or salt(s) thereof present in the solution is in the range of up to about 1.0 mole per mole of said propionic acid and/or salt(s) thereof present in said solution; and wherein said temperature is in the range of from about 100° C. to about 170° C.

26. A method according to claim 25 wherein the inorganic alkali metal base is sodium hydroxide; wherein said excess is in the range of from about 0.2 to about 0.4 mole of sodium cation per mole of said propionic acid and/or salt(s) thereof in the solution.

27. A method according to claim 26 wherein said temperature is in the range of about 120° C. to about 140° C. and said organic nitrogenous base is methylbenzylamine.

\* \* \* \* \*